United States Patent
Ribarov (10) Patent No.: US 10,466,123 B2
(45) Date of Patent: Nov. 5, 2019

(54) EARLY COKING DETECTION IN AIRCRAFT FUEL

(71) Applicant: UNITED TECHNOLOGIES CORPORATION, Farmington, CT (US)

(72) Inventor: Lubomir A. Ribarov, West Hartford, CT (US)

(73) Assignee: UNITED TECHNOLOGIES CORPORATION, Farmington, CT (US)

(*) Notice: Subject to any disclaimer, the term of this patent is extended or adjusted under 35 U.S.C. 154(b) by 132 days.

(21) Appl. No.: 15/627,750

(22) Filed: Jun. 20, 2017

(65) Prior Publication Data

US 2018/0364120 A1 Dec. 20, 2018

(51) Int. Cl.
*G01N 29/02* (2006.01)
*G01N 37/00* (2006.01)
(Continued)

(52) U.S. Cl.
CPC ............ *G01L 9/0025* (2013.01); *F01D 17/02* (2013.01); *F02C 7/22* (2013.01); *F02C 7/222* (2013.01);
(Continued)

(58) Field of Classification Search
CPC ......... G01L 9/00; G01L 9/0025; G01N 29/00; G01N 29/02; G01N 29/024; G01N 29/028;
(Continued)

(56) References Cited

U.S. PATENT DOCUMENTS 5,661,233 A * 8/1997 Spates .................... G01N 11/00
166/250.01
5,798,452 A * 8/1998 Martin .................... G01N 9/002
73/32 R
(Continued)

FOREIGN PATENT DOCUMENTS

DE     102005034449 A1   1/2007
EP       2246698 A1     11/2010
(Continued)

OTHER PUBLICATIONS

European Search Report for Application No./Patent No. 18178901.7-1020 dated Oct. 19, 2018; 7 pgs.
(Continued)

*Primary Examiner* — Nguyen Q. Ha
(74) *Attorney, Agent, or Firm* — Cantor Colburn LLP (57) ABSTRACT

A system and method for detection of coking in a fuel. The system including a fuel system for delivery of fuel, a fuel contamination sensor having a contamination detection sensor with input and output transducers immersed in the fuel, a controller in operable communication with the fuel contamination sensor, the controller configured to execute a method for detection of coking in fuel. The method including generating an excitation signal for the contamination detection sensor, receiving at a controller operably connected to the contamination detection sensor, a sensor output signal from the output transducer, comparing the sensor output signal with the excitation signal, diagnosing a condition of the fuel based on a the comparing, and indicating a condition of coking based on the diagnosing. The system also includes an enunciator to indicate the detection of coking in the fuel.

19 Claims, 7 Drawing Sheets

(51) Int. Cl.
*G01L 9/00* (2006.01)
*F01D 17/02* (2006.01)
*F02C 7/22* (2006.01)
*G01N 29/024* (2006.01)
*G01N 29/036* (2006.01)
*G01N 29/22* (2006.01)
*G01N 29/44* (2006.01)
*G01N 33/28* (2006.01)

(52) U.S. Cl.
CPC ......... *G01N 29/022* (2013.01); *G01N 29/024* (2013.01); *G01N 29/036* (2013.01); *G01N 29/222* (2013.01); *G01N 29/4436* (2013.01); *G01N 33/28* (2013.01); *F05D 2220/32* (2013.01); *F05D 2260/80* (2013.01); *F05D 2270/80* (2013.01); *F05D 2270/806* (2013.01); *G01N 2291/011* (2013.01); *G01N 2291/012* (2013.01); *G01N 2291/014* (2013.01); *G01N 2291/0226* (2013.01); *G01N 2291/0256* (2013.01); *G01N 2291/0258* (2013.01); *G01N 2291/02416* (2013.01); *G01N 2291/0422* (2013.01); *G01N 2291/0423* (2013.01); *G01N 2291/0426* (2013.01)

(58) Field of Classification Search
CPC .... G01N 29/032; G01N 29/036; F01D 17/02; F01D 17/22; F01D 17/222; F05D 2220/32; F05D 2260/80; F05D 2270/806
See application file for complete search history.

(56) References Cited

U.S. PATENT DOCUMENTS 6,534,319 B1 * 3/2003 Liu ................... G01N 1/2226
422/82.01
7,343,804 B2 3/2008 Liu et al.
9,329,154 B1 * 5/2016 Allendorf ............ G01N 29/022
2007/0137287 A1 6/2007 Liu et al.
2010/0115955 A1 5/2010 Goeke et al.
2016/0047790 A1 2/2016 Gaughan et al.
2016/0356224 A1 * 12/2016 Farnum .................. F02C 7/30

FOREIGN PATENT DOCUMENTS

EP 2412953 A2 2/2012
EP 2458179 A2 5/2012

OTHER PUBLICATIONS

Bowers, W.D., Chuan, R. L., Duong, T.M., "A 200 MHz surface acoustic wave resonator mass microbalance", Review of Scientific Instruments, vol. 62, (6), pp. 1624-1629, Jun. 1991; 7 pgs.

Edwards, T., "Liquid Fuels and Propellants for Aerospace Propulsion: 1903-2003", Journal of Propulsion and Power, vol. 19, No. 6, pp. 1089-1107, 2003, 19 pgs.

Edwards, T., Zabarnick, S., "Supercritical Fuel Deposition Mechanisms", Ind. Eng. Chem. Res. vol. 32, pp. 3117-3122, 1993, 6 pgs.

Fromet, M., "Jet Fuel Contamination with FAME (Fatty Acid Methyl Esther)—World Jet Fuel Supply", Airbus Flight Airworthiness Support Technology (FAST) 46, Airbus Technical Magazine, pp. 8-13, Aug. 2010, 40 pgs.

Grate, J.W., Martin, S. J., White, R.M., "Acoustic Wave Microsensors Part 1", Analytical Chemistry, vol. 65, No. 21, Nov. 1, 1993, 9 pgs.

Grate, J.W., Martin, S.J., White, R.M., "Acoustic Wave Microsensors Part II", Analytical Chemistry, vol. 65, No. 22, Nov. 15, 1993, 10 pgs.

Zhu, Y., Yu, C., Zimu, L., Mi, Z., Zhang, X., "Formation of coke in thermal cracking of jet fuel under supercritical conditions", Front. Chem. Eng. China, vol. 2, No. 1, pp. 17-21, 2008, 5 pgs.

* cited by examiner

EARLY COKING DETECTION IN AIRCRAFT FUEL

TECHNICAL FIELD

The present disclosure relates generally to systems and methods for early detection of fuel degradation and fuel coking in a gas turbine engine. More specifically, the present disclosure relates to a method and apparatus for detection of degradation of aircraft fuel when operating at elevated temperatures.

BACKGROUND

Thermal stability of jet fuel is typically described in terms of the fuel's tendency to form deposits on fuel lines, valves, injectors, and combustion chamber surfaces in engines. These fuel system deposits can be created by two distinct free radical pathways: low temperature autoxidation (usually called fouling) and higher temperature pyrolysis (usually called coking or carbon deposition).

Prolonged operation of gas turbine engines at elevated fuel temperatures (say, above 300° F./149° C.) accelerates the fuels reactions that lead to gum and carbon deposit accumulation on various fuel-immersed components such as: fuel filters (increasing the pressure drop across them and reducing the fuel flow); fuel injector orifices (deforming their spray pattern thus leading to localized high-thermal load areas in combustors—i.e. "hot spots"); FMUs (interfering with proper engine controls operability) heat exchangers (reducing the fuel flow and thus heat transfer capabilities), fuel lines (clogging and partially blocking fuel flow); valves, seals, connectors, actuators, etc. These carbon deposits (which have much lower thermal conductivity than typical heat exchanger surface materials and, hence, lower the heat exchangers' capability to conduct heat during this heat exchanger fouling) may lead to higher maintenance costs, more frequent repair/replacements of fuel-immersed components and ultimately, component failures. In general, fuel system fouling inhibits efficient heat transfer which, in turn, results in higher component temperatures and potentially catastrophic component failures.

Oxidative stability (autoxidation) of jet fuel differs from its thermal stability by referring to the rate at which oxygen is consumed and oxidative products are formed. Autoxidation reactions occur during fuel storage and exposure to high temperature in fuel lines which results in a series of liquid oxidation reactions of alkyl radicals generating hydroperoxides and other oxidized products which are believed to be responsible for solid deposit formation.

Autoxidation lowers the jet fuel's quality from the amount of gaseous oxygen dissolved into fuel which, in turn, lowers the fuel's thermal sink capabilities.

Other organic contaminants such as FAME (Fatty Acid Methyl Esters) that come from bio-diesel fuels and from cross-contamination during refueling of aircraft from ground-based fuel tankers/bowsers can also pose significant fuel quality problems. Additional accumulation of organic acids due to oxidation of fuel hydrocarbons can occur during the handling of fuel. The resulting carboxylic acids are corrosive to some metals and can increase the solubility of these metals in fuel. Any fuel system components which consist of such metals are likely to be eroded and damaged. Organic acids can increase carbon deposition in fuel and can have negative effect on the fuel's thermal stability and the fuel system's components' material compatibility. Some existing techniques for detection of coking/varnishing in aircraft jet fuel systems rely on many temperature sensors placed around the gas turbine engine to predict when fuel degradation will happen. While these methods may be effective, it is would be advantageous to employ a more effective accurate means of early detection and warning of fuel coking in aviation fuels at elevated operational fuel temperatures.

BRIEF DESCRIPTION

According to one embodiment of the invention, described herein is a system and method for detection of coking in a fuel. The system including a fuel system for delivery of fuel, a fuel contamination sensor having a surface acoustic wave (SAW) sensor with input and output transducers immersed in the fuel, a controller in operable communication with the fuel contamination sensor, the controller configured to execute a method for detection of coking in fuel. The method including generating an excitation signal for the SAW sensor, receiving at a controller operably connected to the SAW sensor a sensor output signal from the output transducer, comparing the sensor output signal with the excitation signal, diagnosing a condition of the fuel based on a the comparing, and indicating a condition of coking based on the diagnosing. The system also includes an enunciator to indicate the detection of coking.

In addition to one or more of the features described above, or as an alternative, further embodiments may include that the generating includes providing an alternating current (AC) signal to the contamination detection sensor.

In addition to one or more of the features described above, or as an alternative, further embodiments may include that the alternating current (AC) signal is at least one of a sinusoid and exhibits a frequency corresponding to the synchronous frequency of the contamination detection sensor to minimize insertion loss.

In addition to one or more of the features described above, or as an alternative, further embodiments may include that the contamination detection sensor is at least one of a surface acoustic wave sensor, a horizontal shear acoustic wave sensor, and a thickness shear mode sensor.

In addition to one or more of the features described above, or as an alternative, further embodiments may include that the sensor output signal exhibits at least one of a delay, a phase shift, a frequency shift based on a presence of particulates in the aircraft fuel.

In addition to one or more of the features described above, or as an alternative, further embodiments may include that the at least one of a delay, a phase shift, and a frequency shift is proportional to the mass of a particle or film deposited on the sensor in the aircraft fuel.

In addition to one or more of the features described above, or as an alternative, further embodiments may include that the diagnosing includes at least one of collecting data over time to facilitate making lifetime predictions of fuel system component, and identifying coking only after a predetermined threshold of coking has been exceeded.

In addition to one or more of the features described above, or as an alternative, further embodiments may include that the identifying includes latching an indication of detected coking and notifying a ground maintenance to conduct and inspection of the fuel system.

In addition to one or more of the features described above, or as an alternative, further embodiments may include that the fuel system components include at least one of sensors, valves, tubing nozzles, and injectors.

Also described herein in an embodiment is a system for early detection of coking in aircraft fuel. The system includes a fuel system for delivery of fuel to a component, a fuel contamination sensor, the fuel contamination sensor having an input transducer and an output transducer immersed in the aircraft fuel, and a controller in operable communication with the fuel contamination sensor, the controller configured to execute a method for early detection of coking m the aircraft fuel. The method includes generating an excitation signal for the contamination detection sensor, receiving at a controller operably connected to the contamination detection sensor a sensor output signal from the output transducer, comparing the sensor output signal with the excitation signal, diagnosing a condition of the fuel based on a the comparing, and indicating a condition of coking based on the diagnosing. The system also includes an enunciator to indicate the detection of coking.

In addition to one or more of the features described above, or as an alternative, further embodiments may include that the excitation signal is an alternating current (AC) signal to the contamination detection sensor.

In addition to one or more of the features described above, or as an alternative, further embodiments may include that the alternating current (AC) signal is at least one of a sinusoid and exhibits a frequency corresponding to the synchronous frequency of the contamination detection sensor to minimize insertion loss.

In addition to one or more of the features described above, or as an alternative, further embodiments may include that the contamination detection sensor is at least one of a surface acoustic wave sensor, a horizontal shear acoustic wave sensor, and a thickness shear mode sensor.

In addition to one or more of the features described above, or as an alternative, further embodiments may include that the sensor output signal exhibits at least one of a delay, a phase shift, a frequency shift based on a presence of at least one of particulates or film disposed on the contamination detection sensor in the aircraft fuel.

In addition to one or more of the features described above, or as an alternative, further embodiments may include that the output signal of the sensor exhibits at least one of a delay, a phase shift, and a frequency shift proportional to the mass of a particle or film deposited on the sensor in the aircraft fuel.

In addition to one or more of the features described above, or as an alternative, further embodiments may include that the diagnosing includes at least one of collecting data over time to facilitate making lifetime predictions of fuel system component, and identifying fuel coking only after a predetermined threshold of fuel coking has been exceeded.

In addition to one or more of the features described above, or as an alternative, further embodiments may include that the identifying includes latching an indication of detected fuel coking and notifying a ground maintenance to conduct and inspection of the fuel system.

In addition to one or more of the features described above, or as an alternative, further embodiments may include that the fuel system components include at least one of sensors, valves, filters, screens, pumps, piping, tubing nozzles, and injectors.

In addition to one or more of the features described above, or as an alternative, further embodiments may include that at least a portion of the fuel system is used as a heat sink.

In addition to one or more of the features described above, or as an alternative, further embodiments may include that the fuel system is part of a gas turbine engine.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE DRAWINGS

The subject matter which is regarded as the disclosure is particularly pointed out and distinctly claimed in the claims at the conclusion of the specification. The foregoing and other features, and advantages of the disclosure are apparent from the following detailed description taken in conjunction with the accompanying drawings in which:

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. The following description is merely illustrative in nature and is not intended to limit the present disclosure, its application or uses. It should be understood that throughout the drawings, corresponding reference numerals indicate like or corresponding parts and features. As used herein, the term controller refers to processing circuitry that may include an application specific integrated circuit (ASIC), an electronic circuit, an electronic processor (shared, dedicated, or group) and memory that executes one or more software or firmware programs, a combinational logic circuit, and/or other suitable interfaces and components that provide the described functionality.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection".

As shown and described herein, various features of the disclosure will be presented. Various embodiments may have the same or similar features and thus the same or similar features may be labeled with the same reference numeral, but preceded by a different first number indicating the figure to which the feature is shown. Thus, for example, element "a" that is shown in Figure X may be labeled "Xa" and a similar feature in Figure Z may be labeled "Za." Although similar reference numbers may be used in a generic sense, various embodiments will be described and various features may include changes, alterations, modifications, etc. as will be appreciated by those of skill in the art, whether explicitly described or otherwise would be appreciated by those of skill in the art.

It is desirable to provide an early detection method that detects the occurrence of coking in aircraft fuels. In general, embodiments herein relate generally to a system and method to detect when coking is actually beginning to occur in the fuel. Described herein is a sensor and method for employing Surface Acoustic Wave sensing techniques to detect the formation of film or particulates in the fuel in high temperature applications. This approach provides more accurate results than legacy systems that predict coking as a function of detected temperatures in the fuel.

Figure 1:
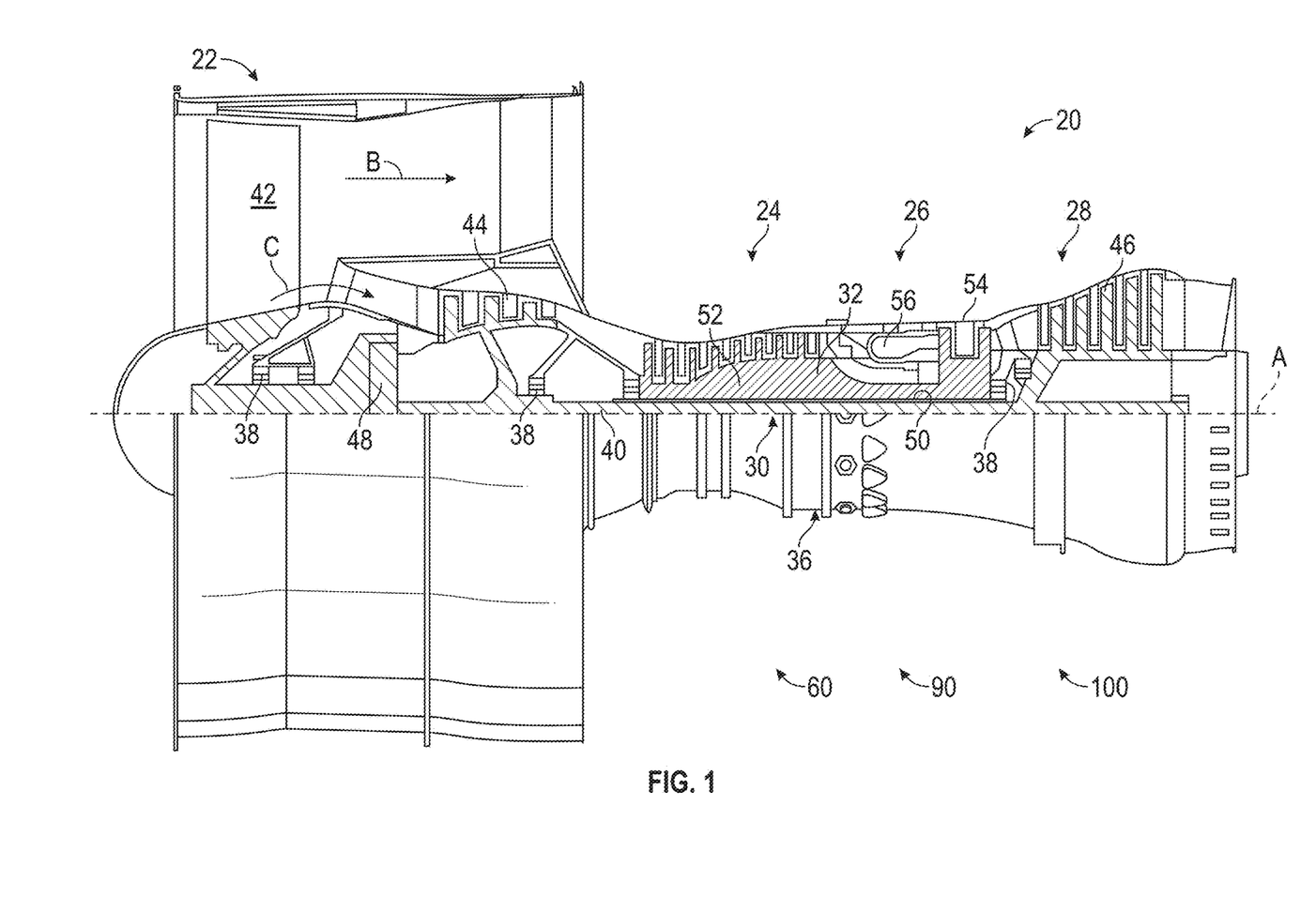
FIG. 1 depicts a simplified partial cutaway of a gas turbine engine as employed in the embodiments.

FIG. 1 schematically illustrates a gas turbine engine 20. The gas turbine engine 20 is disclosed herein as a two-spool turbofan that generally incorporates a fan section 22, a compressor section 24, a combustor section 26 and a turbine section 28. Alternative engines might include an augmentor section (not shown) among other systems or features. The fan section 22 drives air along a bypass flow path B in a bypass duct, while the compressor section 24 drives air along a core flow path C for compression and communication into the combustor section 26 then expansion through the turbine section 28. Although depicted as a two-spool turbofan gas turbine engine in the disclosed non-limiting embodiment, it should be understood that the concepts described herein are not limited to use with two-spool turbofans as the teachings may be applied to other types of turbine engines including three-spool architectures.

The gas turbine engine 20 generally includes a low speed spool 30 and a high speed spool 32 mounted for rotation about an engine central longitudinal axis A relative to an engine static structure 36 via several bearing systems 38. It should be understood that various bearing systems 38 at various locations may alternatively or additionally be provided, and the location of bearing systems 38 may be varied as appropriate to the application.

The low speed spool 30 generally includes an inner shaft 40 that interconnects a fan 42, a low pressure compressor 44 and a low pressure turbine 46. The inner shaft 40 is connected to the fan 42 through a speed change mechanism, which in exemplary gas turbine engine 20 is illustrated as a geared architecture 48 to drive the fan 42 at a lower speed than the low speed spool 30. The high speed spool 32 includes an outer shaft 50 that interconnects a high pressure compressor 52 and high pressure turbine 54. A combustor 56 is arranged in exemplary gas turbine 20 between the high pressure compressor 52 and the high pressure turbine 54. An engine static structure 36 is arranged generally between the high pressure turbine 54 and the low pressure turbine 46. The engine static structure 36 further supports bearing systems 38 in the turbine section 28. The inner shaft 40 and the outer shaft 50 are concentric and rotate via bearing systems 38 about the engine central longitudinal axis, which is collinear with their longitudinal axes.

The core airflow is compressed by the low pressure compressor 44 then the high pressure compressor 52, mixed and burned with fuel in the combustor 56, then expanded over the high pressure turbine 54 and low pressure turbine 46. The turbines 46, 54 rotationally drive the respective low speed spool 30 and high speed spool 32 in response to the expansion. It will be appreciated that each of the positions of the fan section 22, compressor section 24, combustor section 26, turbine section 28, and fan drive gear system 48 may be varied. For example, geared architecture 48 may be located aft of combustor section 26 or even aft of turbine section 28, and fan section 22 may be positioned forward or aft of the location of gear system 48.

The aircraft engine 20 in one example is a high-bypass geared turbofan engine. In a further example, the engine 20 bypass ratio is greater than about six (6), with an example embodiment being greater than about ten (10), the geared architecture 48 is an epicyclic gear train, such as a planetary gear system or other gear system, with a gear reduction ratio of greater than about 2.3 and the low pressure turbine 46 has a pressure ratio that is greater than about five. In one disclosed embodiment, the engine 20 bypass ratio is greater than about ten (10:1), the fan diameter is significantly larger than that of the low pressure compressor 44, and the low pressure turbine 46 has a pressure ratio that is greater than about five 5:1. Low pressure turbine 46 pressure ratio is pressure measured prior to inlet of low pressure turbine 46 as related to the pressure at the outlet of the low pressure turbine 46 prior to an exhaust nozzle. The geared architecture 48 may be an epicycle gear train, such as a planetary gear system or other gear system, with a gear reduction ratio of greater than about 2.3:1. It should be understood, however, that the above parameters are only exemplary of one embodiment of a geared architecture engine and that the present disclosure is applicable to other gas turbine engines including direct drive turbofans.

The engine 20 may typically employ a variety of subsystems for operation. For example in an embodiment the engine 20 may employ a fuel subsystem shown generally as 60, electrical and sensing subsystems, shown generally as reference numeral 90, a control subsystem shown generally as 100, and the like. A fuel subsystem 60 may include the various tubing, piping, filters, screens, controls, pumps, valves, sensors and the like employed to deliver fuel as required for engine operation under a variety of conditions. The engine 20 may include and electronic engine control (EEC) system 100. Electronic engine control system 100 may include controls and interfaces for actuators, sensors and the like and a controller. For example, the control system 100 could be a Full Authority Digital Engine Control (FADEC) system. Further details on the control system 100 and the control processing are presented in detail below. Electrical and sensor subsystems 90 may interface with the fuel subsystem 60 and control system 100 in any of a variety ways to detect and measure the operation of the engine 20. The sensors employed in the engine 20 may include, but not be limited to temperature, pressure, flow, speed and position sensors, a contamination sensor in accordance with an embodiment, and the like.

Typically in operation, fuel is employed in a variety of applications as it is routed to the engine 20 and to the combustor 56 to be mixed with compressed air to be burned. One application commonly employed in gas turbine engines is to use the fuel as a heat sink. Advantageously, because of the thermal properties of fuel, it provides far more effective heat sinking performance than other techniques such as conduction to the engine 20 or aircraft frame, or use of air for cooling. In addition, in some applications, other techniques for dissipating heat may be limited or may not be available or may be too cumbersome to implement. Therefore, commonly, the incoming fuel becomes a very practical selection for cooling where the fuel subsystem 60 includes routing, piping, tubing, manifolds, and the like around the engine 20 to facilitate this application. However, as a result of using the fuel in a heat sinking capacity, the temperature of the fuel is increased by these various thermal applications, before it arrives at the combustor 56. In addition, the operating environment of the gas turbine engine 20 can be extremely hot, exceeding, 750° F./400° C. in some areas. As a result, as the fuel is routed to the combustor 56 it is also heated by the hot ambient environment of the engine 20. As discussed earlier, prolonged operation of gas turbine engines at elevated fuel temperatures (say, above 300° F./149° C.) accelerates the fuel's reactions that lead to gum as well as carbon deposit accumulation on various fuel-immersed components. Most importantly, such build up can interfere with fuel injector orifices deforming their spray pattern thus leading to localized high-thermal load areas in combustors i.e., "hot spots". Such undesirable thermal gradients inside the combustor can lead to increased pattern factors (PFs) which can shorten the life of the combustor. (A PF is generally defined as $PF=(T4_{peak}-T4_{avg})/T4_{avg}$, where T4 is the combustor exit temperature. The objective is to reduce PF and thus achieve a more uniform, two-dimensional temperature profile at the exit of the combustor.) These unwanted fuel coking deposits may lead to higher maintenance costs, more frequent repair/replacements of fuel-immersed components and ultimately, if component failures.

Figure 2:
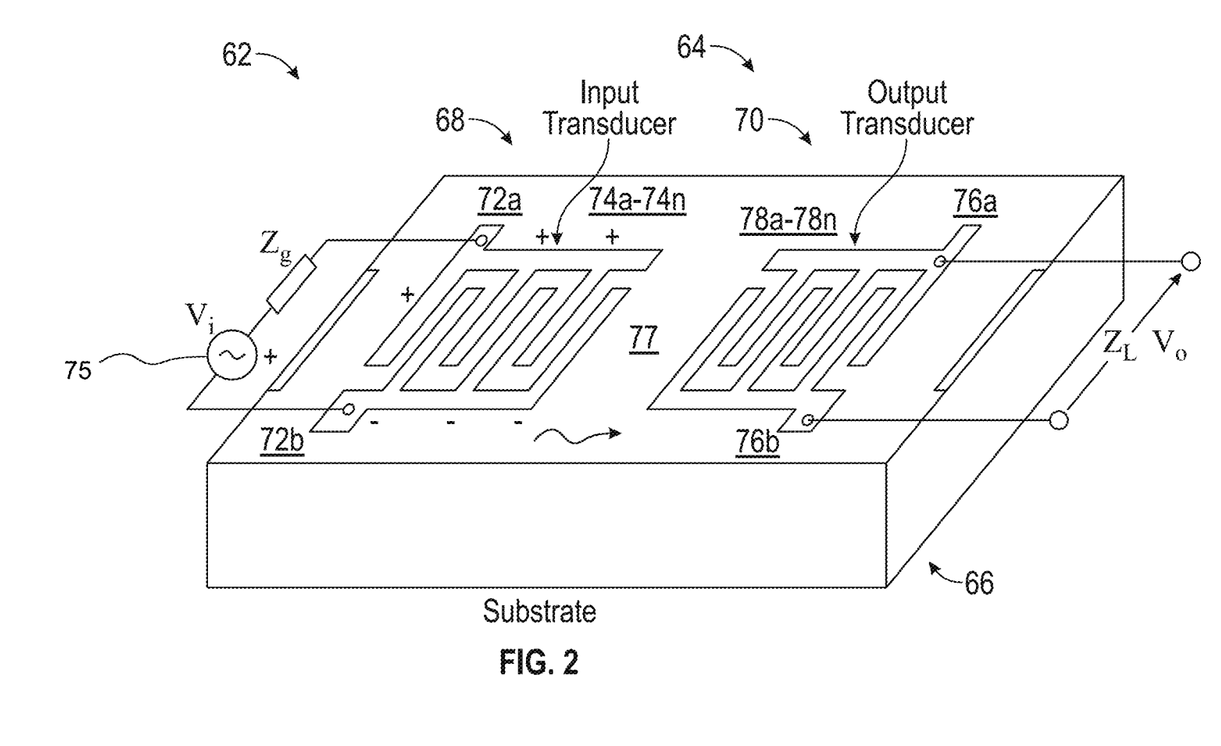
FIG. 2 is a simplified block diagram of Surface Acoustic Wave sensor in accordance with an embodiment.

FIG. 2 depicts a contamination detection sensor 62 in accordance with an embodiment. In an embodiment the contamination detection sensor 62 utilizes a compact acoustic wave sensing structure and system 64, which detects small changes in mass loads due to coking deposits in the "dirty" jet fuel. In one embodiment, a surface acoustic wave (SAW) structure is employed. Any fuel-borne particulates (i.e., soot, char, varnish, etc.) are collected on the SAW sensing structure 64. In an embodiment, the acoustic wave sensing structure and system 64 is incorporated with a fuel plug/dip 63 (FIGS. 5A & 5B) or as a separate component. Any fuel contamination/debris accumulation can be readily detected when the plug 63 with attached to the acoustic wave sensing structure 64 is periodically removed and inspected, as, for example, during routine ground crew inspection, maintenance checks, testing, and the like.

Acoustic wave sensors are a class of microelectromechanical systems (MEMS) which rely on the modulation of surface acoustic waves to sense a physical phenomenon. The term "acoustic wave sensor" may include (but is not limited to) a variety of related MEMS sensor architectures such as surface acoustic wave (SAW), thickness-shear mode (TSM), surface transverse wave (STW), flexural plate wave (FPW), acoustic plate mode (APM), shear-horizontal surface acoustic wave (SH-SAW), shear-horizontal acoustic plate mode (SH-APM), Love wave, Lamb wave, surface skimming bulk wave (SSBW), etc. The sensor transduces an input electrical signal into a mechanical wave which, unlike an electrical signal, can be easily influenced by physical phenomena. The device then transduces this wave back into an electrical signal. Changes in amplitude, phase, frequency, or time-delay between the input and output electrical signals can be used to measure the presence of the detected phenomenon. In this instance, the presence of particulates in the fuel, or a buildup of a film or deposits indicating that coking is occurring.

As depicted in FIG. 2, the SAW sensing structure and system 64 includes of a piezoelectric substrate 66, an input transducer (IDT) 68 with two electrodes 72a, 72b having a plurality of interdigitated fingers 74a-74n (alternating interspersed fingers for two sides of the transducer 68) at one end of one side of the surface of the substrate 66, and a second, interdigitated output transducer 70 with electrodes 76a, 76b and fingers 78a-78n on the other end of that surface of the substrate 66. The space between the two transducers 68 and 70, across which the surface acoustic waves propagate, is known as the delay-line 77. This region is called the delay line 77 because the acoustic signal, which is a mechanical wave at this point, moves much slower than its electromagnetic form, thus causing an appreciable delay.

In operation the SAW sensor structure and system 64 uses the input transducer 68 to convert an electrical signal into an acoustic wave. An AC electrical input signal generated by an excitation source 75 creates alternating polarity between the fingers 74a-74n of the interdigitated input transducer 68. Between two adjacent sets of fingers 74a-74n, polarity of the fingers 74a-74n will be switched (e.g. + − +). As a result, the direction of the electric field between two fingers 74a-74n will alternate between adjacent sets of fingers 74a-74n. This creates alternating regions of tensile and compressive strain between fingers 74a-74n of the electrodes 72a, 72b by the piezoelectric effect, producing a mechanical wave at the surface known as a surface acoustic wave. This is a Rayleigh wave which radiates in both directions (i.e. parallel and normal) away from the input transducer 68 with waveforms parallel to the lengths of the interdigitated fingers 74a-74n. As fingers 74a-74n on the same side of the device will be at the same level of compression or tension, the space between them—known as the pitch—is the wavelength of the mechanical wave. The synchronous frequency is the natural frequency at which mechanical waves should propagate. Ideally, the input electric signal should be at the synchronous frequency to minimize insertion loss.

As the mechanical wave propagates from the input transducer 68, energy of the waveform will propagate across the delay line 77 in the direction of the output transducer 70. The acoustic wave travels across the surface of the device substrate 66 to the output transducer 70, which converts the wave back into an electric signal for measurement. As may be appreciated, any changes that were made to the mechanical wave (e.g., changes in wave velocity, frequency, amplitude, etc.) will be reflected in the measured output electric signal from the output transducer 70. As the characteristics of the surface acoustic wave can be modified by changes in the surface properties of the device substrate 66, the SAW sensor structure and system 64 can be designed and configured to quantify any variety of phenomena which alter these properties. Typically, this is accomplished by the addition of mass to the surface or changing the length of the substrate 66 and the spacing between and quantity of the fingers 74a-74n, 78a-78n.

In another embodiment of the contamination detection sensor 62, the SAW sensor structure and system 64 can be configured and implemented as a film thickness sensor. That is, if the SAW sensor structure and system 64 is not coated with an adhesive substance, as described with respect to an earlier embodiment, then the SAW sensor structure and system 64 operates as a film thickness sensor. In this way, the measured wave exhibits a frequency shift from the source frequency, proportional to the mass of a deposited film on the sensor. Therefore, the sensor measures the film density and acoustic impedance to provide film thickness data. Once again, the deposition of a film on the contamination detection sensor 62 being indicative of coking in the fuel.

Various piezoelectric substrates 66 can be used for manufacturing of the SAW sensor structure and system 64 of the described embodiments. These substrates 66 include, but are not limited to: quartz ($SiO_2$), silicon carbide (SiC), lithium tantalite ($LiTaO_3$), lithium nobiate ($LiNbO_3$), gallium arsenide (GaAs), langasite (LGS), zinc oxide (ZnO), aluminum nitride (AlN), lead zirconium titanite (PZT), polyvinylidene fluoride (PVDF), and the like.

Figure 3:
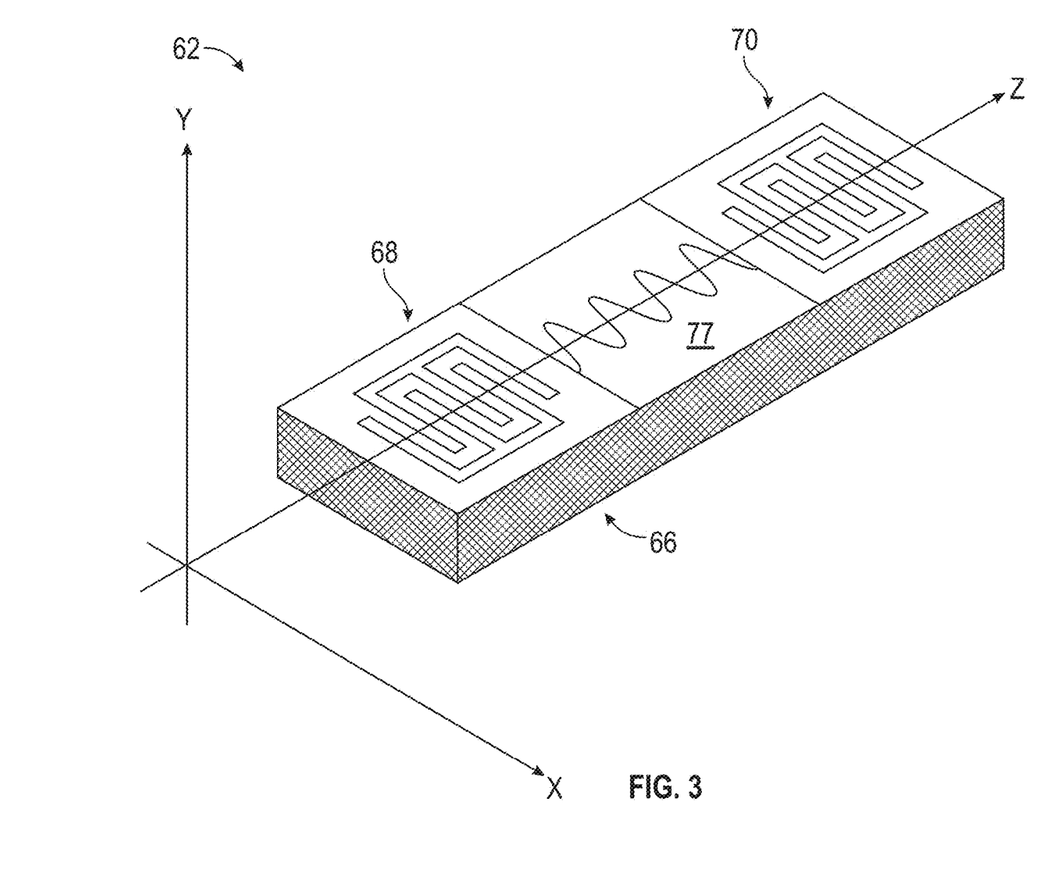
FIG. 3 is a simplified block diagram of Shear-Horizontal Surface Acoustic Wave sensor in accordance with an embodiment.

Turning now to FIG. 3, a horizontal shear SAW sensor in accordance with an embodiment is depicted. In an embodiment, the SH-SAW structure and system are the same as described above with respect to the SAW structure and system 64 except as follows. In an embodiment, by selectively orienting the cut of the piezoelectric substrate (66) crystal material of a typical SAW sensor structure and system 64, a SH-SAW sensor is achieved. This configuration changes the wave propagation mode from vertical shear as is typical for a SAW sensor to horizontal shear (SH-SAW sensor) as depicted. Advantageously, this modification significantly reduces the energy losses in an incompressible medium (i.e., liquid). As result, the SH-SAW type sensor may exhibit advantages in implementation in such applications. Otherwise, the operational characteristics of a SH-SAW sensor are nearly identical to the ones of the SAW sensor structure and system 64.

Figure 4:
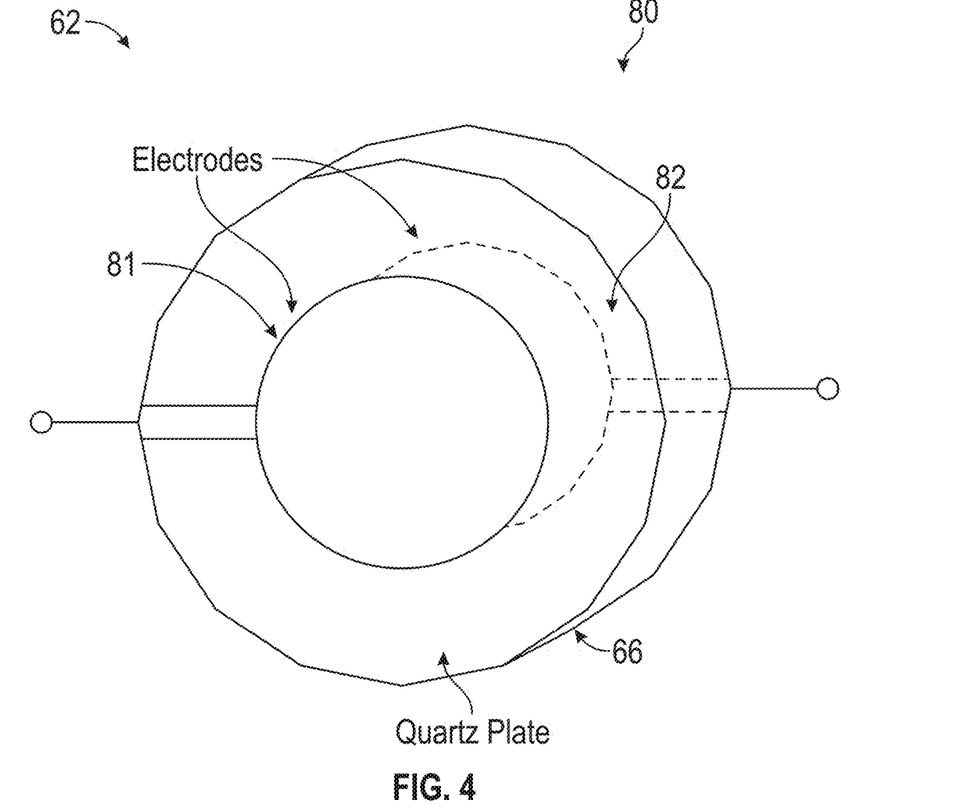
FIG. 4 is a simplified block diagram of Thickness Shear Mode sensor in accordance with an embodiment.

Advantageously, for a simpler device where lower accuracy is acceptable for the application, the contamination detection sensor 62 may be operated as a thickness shear mode (TSM) resonator. TSM sensors have several advantages such as: simplicity of manufacture, temperature stability, capability to withstand harsh environments, and relatively good sensitivity. Turning now to FIG. 4 where a simplified illustration of the contamination detection sensor 62 is depicted with a TSM resonator 80 as the sensing structure. The acoustic waves generated in TSM resonators 80 are bulk transverse waves which travel in a direction perpendicular to the surface of the plate. As a result, particle displacements are parallel to the surface, i.e. "in-plane" displacements. These "in-plane" particle motions dissipate energy into the medium mostly by viscous coupling, thus making the energy losses relatively low. Hence, a TSM resonator 80 based sensor may be especially suitable for applications in incompressible media (i.e., liquids). Unlike SAW sensors, which operate at much higher resonant frequencies (say around 30-500 MHz.), the resonant frequencies of the typical TSM sensors are around 5-10 MHz.

Like the operation of the SAW sensor structure and system 64 the TSM resonator 80 uses an input transducer 81 to convert an electrical signal into an acoustic wave. An AC electrical input signal generated by an excitation source (not shown) just as with the SAW sensor. Once again, the synchronous frequency is the natural frequency at which mechanical waves should propagate. Ideally, the input electric signal should be at the synchronous frequency to minimize insertion loss. As the mechanical wave propagates from the input transducer 81, energy of the waveform will propagate into the medium (fuel) and then detected by an output transducer 82, which converts the wave back into an electric signal for measurement. As with the previous sensors, any changes that were made to the mechanical wave (e.g., changes in wave velocity, frequency, amplitude, etc.) will be reflected in a measured output electric signal from the output transducer 82. Similar to SAW sensors the characteristics of the bulk transvers waves can be modified by changes in the properties of the device substrate 66, the TSM sensor structure 80 can be designed and configured to quantify any variety of phenomena which alter these properties. Typically, this is accomplished by the addition of mass to the surface or changing the size and characteristics of the substrate 66.

In general, mass sensitivity increases as the detected mass per unit area of the sensor/detector decreases. The thickness of the sensor plate of a SAW sensor is the penetration depth of the waves. This depth is smaller than the acoustic wavelength which makes the detected mass per unit area of the SAW sensor very small. This, in turn, results in very high mass sensitivity for the SAW sensor. As a result, the thickness of the sensor plate of a SAW sensor is much smaller than the value of the detected wavelength.

On the other hand, the sensing plate thickness, d, of TSM sensors is about ½ of the detected wave's wavelength, λ, in the substrate material. As a consequence, in general, TSM sensors have very thin sensing plates to achieve the desired mass sensitivity to be effective as a particle or film detector. TSM sensors can be made more sensitive by decreasing their sensing plate thickness. This, however, leads to a more fragile device whose structure (i.e., really thin sensing plate) is difficult to support/integrate into a sensing device and structure.

For example, for a quartz-based substrate (wave propagation speed, v, is about 3300 m/s), at a frequency of about f=5 MHz, for example, the resulting wavelength, λ is: =660 μm. Therefore, the sensing plate thickness, d, is d=½(λ) =330 μm. This results in an extremely thin plate.

However, in some applications, implementation is possible. For a practical application as the contamination detection sensor 62, a thicker sensing plate with improved rigidity can prove to be quite viable as a sensor (albeit with the expected decreased mass sensitivity). In fact, decreasing mass sensitivity may be advantageous as it may limit the number of "nuisance" faults (i.e., detection of some "minute" fuel coking particles which may be causing a premature issue a "fuel coking" conditions command) during normal operation of the fuel system. Thus a thicker sensing plate for the TSM sensor, would in turn, improves the TSM sensor's installation capability, as well as its operability and durability.

Figure 5A:
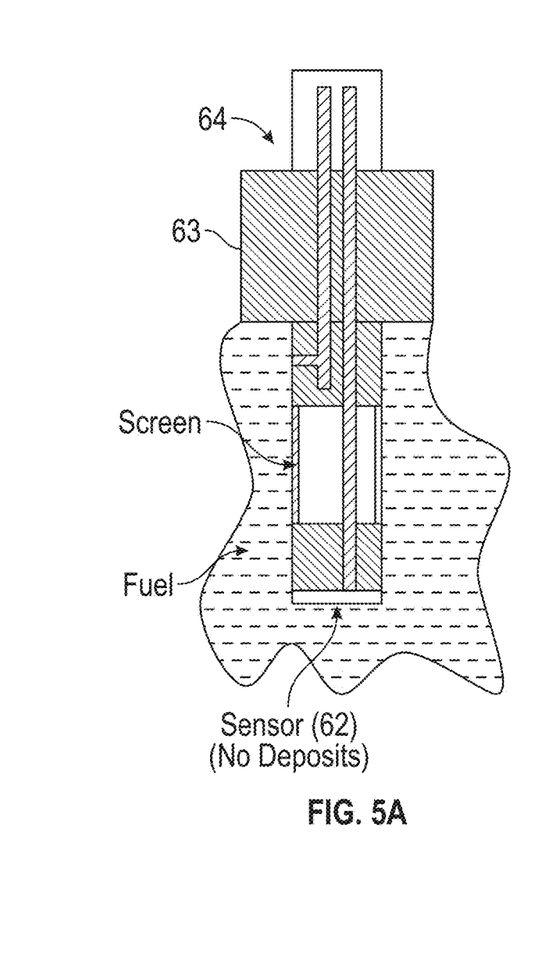
FIG. 5A is a simplified depiction of a contamination detection sensor without contamination in accordance with an embodiment.
Figure 5B:
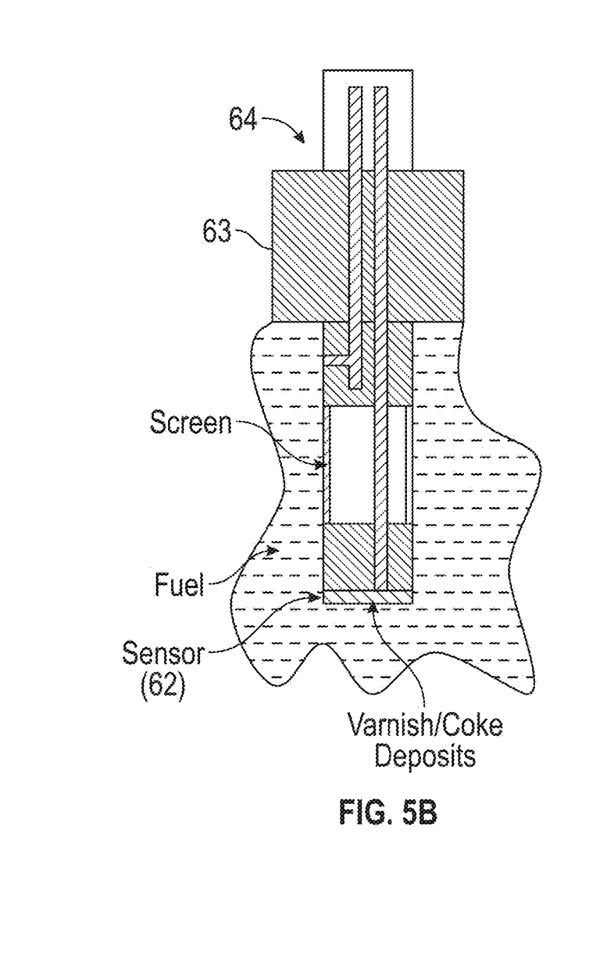
FIG. 5B is a simplified of a contamination detection sensor with contamination in accordance with an embodiment.

Turning now to FIGS. 5A and 5B where an embodiment of the fuel contamination sensor 62 employing the SAW sensor structure and system 64 as may be employed in application. FIG. 5A depicts the fuel contamination sensor 62 implemented as a sensor or plug 63 immersed in the aircraft engine fuel system 60 with no contamination or deposits, while FIG. 5B depicts the fuel contamination sensor 62 immersed in the aircraft engine fuel system 60 (FIG. 1) with film, deposits, contamination and the like amassed on the contamination sensor 62. In an embodiment the SAW sensor structure and system 64 is implemented at the base of the plug 63. In an embodiment, the SAW sensor structure and system 64 can be configured in several distinct ways for detection of coking in fuels. In an embodiment, the contamination detection sensor 62 may be configured as a particulate sensor. That is, if the contamination detection sensor 62 is coated with an adhesive substance, then any non-liquid particulate landing on the coated surface of the sensor will perturb its surface acoustic wave propagation resulting in detection of the particulate matter. Advantageously, extremely high mass resolution (on the order of 3 picograms (pg) for a 200-MHz SAW sensor have been achieved.

Due to its wave's surface-normal component, the SAW sensor structure and system 64 is particularly suitable for use in gaseous environments, since this sensor type radiates compression waves into the medium. For a compressible medium (such as gas/vapor) this effect is negligible, while signal attenuation can occur in incompressible medium (i.e., liquid). Hence, the proposed SAW sensor structure and system 64 can also be used as a detector of gas in the liquid fuel in conditions where unwanted two-phase (i.e., vapor and liquid phases) flow may be occurring. Two-phase flow may result from air dissolved into fuel (due to aging of fuel or exposure of fuel to low ambient pressures such as at high flight altitudes). Another undesirable two-phase flow occurrence may result from fuel cavitation near/around high-speed fuel pumps. Such two-phase flow occurrences in fuel are detrimental to the proper operation of fuel systems. As a result, the fuel's propensity for thermal break-down is increased, which in turn, limits the fuel's heat sink capabilities. Therefore, it is desirable to be able to detect the onset or presence of such two-phase flow occurrences as early and as accurately as possible. The proposed SAW sensor structure and system 64 can be utilized for this capability as well.

Figure 6:
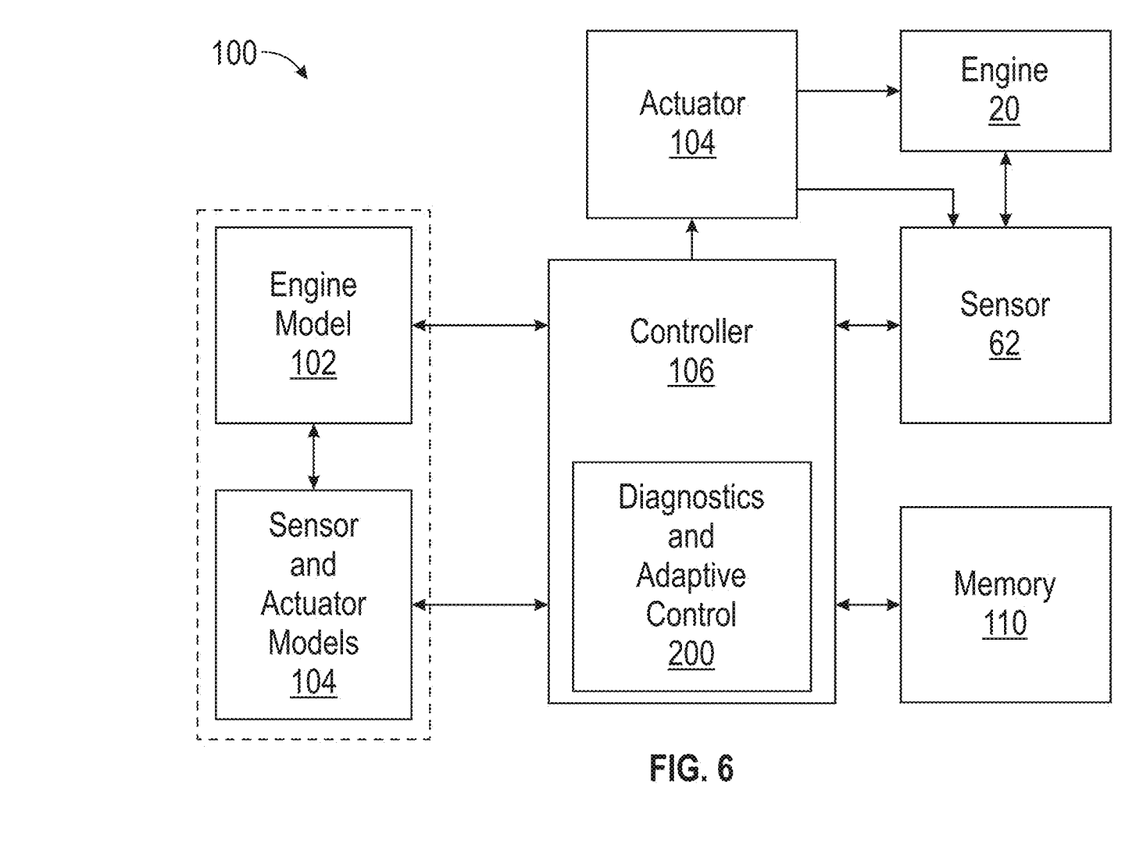
FIG. 6 is a simplified block diagram of an engine control system in accordance with an embodiment.

FIG. 6 illustrates an exemplary embodiment of an engine control system 100 including optional model based control, as may be employed with engine 20. As shown in FIG. 6, system 100 includes engine 20, an actuator 114 and a sensor 62 that is communicatively coupled with a processor or controller 106. In an embodiment, sensor 62 is any of a variety of sensor employed in the engine including temperature, pressure, flow, speed and position sensors, and the like. In this embodiment, and for the purposes of description of the embodiments herein, the sensor 62 is a contaminant detection sensor associated with detecting debris due to fuel coking in the fuel supplied to the engine. Other types of suitable sensors (e.g., flow meters and speed sensors) could also be used.

In operation of the engine 20, the processor 106 is communicatively coupled to the actuator 114 to provide commands to control the engine 20. In addition optionally, the processor 106 is operatively coupled to a memory 110, sensor and actuator models 104, and an engine model 102. The sensor and actuator models 104 are associated with any of the sensor(s) 62 and actuator(s) 114, and, in this embodiment, are communicatively coupled with the engine model 102. Alternatively, functionality associated with a sensor and actuator models 104 may be an integrated with an engine model 102 in other embodiments to form a system model. Further, in other embodiments, engine model(s) 102 and/or sensor and actuator model(s) 104 may be integrated into various components such as, for example, into an Electronic Engine Control (EEC) system, such as a Full Authority Digital Engine Control (FADEC) system such as system 100. In an exemplary embodiment, the FADEC may be physically attached to the gas turbine engine 20.

In operation, the sensor 62 monitors an engine or operating parameter, such as temperature, pressure, vane or actuator position, and the like, and provides data corresponding to the parameter to the processor 106, which may store the data in memory 110. The processor 106 processes the data stored in the memory 110 and employs the data in various control algorithms and diagnostics. In some embodiments, where model based control is employed, the processor 106 compares from the sensor 62 to corresponding data of the sensor and actuator model 104. If the difference between the measured data of the sensor 62 and the reference data of the actuator model 104 is outside of a threshold value, the processor 106 may take various steps to address the difference including update the sensor and actuator model 104 with the data of the sensor 62, ignoring the difference between measured data and model data or other mitigation steps as discussed further herein. In addition, in an embodiment, by updating the reference data of the actuator model 104, degradation of the actuator 114, which may occur over time, can be accommodated.

Monitoring engine parameter data provides the basis for performing gas turbine engine performance tracking. The dynamic behavior of measurement devices, particularly detecting and quantifying the changes in the dynamic responses of measurement devices, is useful in performing gas turbine engine performance tracking. By monitoring sensors data based on transient behavior, steady-state behavior and trend data, degradation of engine actuators 114 may be detected that may not be perceived when the engine is operating at steady-state alone. Ascertaining and distinguishing degraded performance trends may allow the engine model 102 and sensor and actuator model 104 to be updated in order to compensate for sensor degradation.

Using model-based control(s) allows the control system 100 to use all the information provided by the system model 102, 104, estimator, and diagnostic and adaptive control processes 200. The algorithm used herein allows the controller 106 to see what the engine is going to do over time and at the same time know the engine operating constraints. The control system 100 can then modify selected control actions to ensure that the constraints are not violated while satisfying a given control objective. In other words the control ideally can develop an improved, if not the best possible, solution to meet the mission requirements within the constraints presented.

The role of the diagnostics in the described embodiments is to detect, isolate, and identify any deterioration or degradation, fault, failure, or damage in the gas turbine engine system 20. In some embodiments, the diagnostic and adaptive control method 200 may be based on model-based diagnostics, or multi-model based diagnostics, where information from the other control components like the engine model 102 sensor model 104, and model structure, innovations, parameter updates, states, sensor values, sensor estimates, etc. are used to diagnose the engine and components. With such information, the diagnostics can determine if there is a fault, where the fault is located, and the magnitude of the fault, and then the controller can adjust the operation of the control system 100 accordingly.

Figure 7:
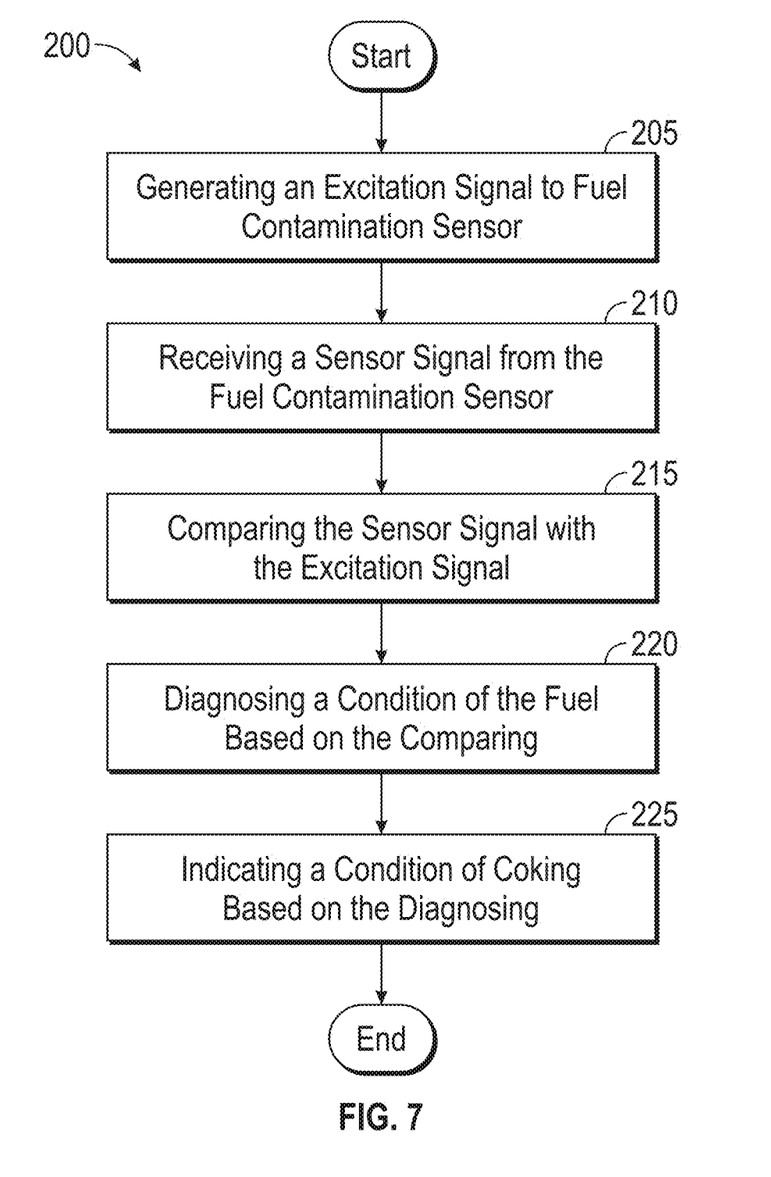
FIG. 7 depicts a flowchart of the method early detection of fuel coking in accordance with an embodiment.

FIG. 7 depicts one of the diagnostic processes for observing data for a component, sensor 62 and then employing the data in the control system 100. While in an embodiment description is made with reference to a sensor 62, other components and systems, including sensors 62 and actuators 114 may be applicable. In an embodiment, the diagnostic process performs a method for detection and diagnosis of a subsystem fault (related to temperature, pressures, and statuses such as detecting coking) of an engine fuel system by trending their measured response. The control system 100 then adapts to the detected fault or degradation to improve performance of the control system 100 and the operation of the engine 20. In an embodiment the diagnostics and adaptive control method 200 includes, but is not limited to logic for identifying the fault in the fuel or fuel system by comparing measured temperatures, pressures and status of detections sensor with those corresponding to healthy or nominal engine performance values. These algorithms that can be executed periodically, similar to a Built-In-Test (BIT) or more often depending on the testing and data, particularly during selected operational regimes. For example, during operation of the engine 20, tests conducted to evaluate the temperatures, pressures and status may be conducted. In addition, during selected operational regimes of the engine 20 data may be collected on the current operation of fuel system and engine 20 to supplement and build trend data. The type of faults and degradation of the engine performance to be identified may be based on system responses to predetermined commands, modeled expected behavior, constraints or limits of operation and the like. Such algorithms can identify specific parameters associated with the engine and fuel subsystem models trend them using historical data, and map them to specific failures.

Continuing now with FIG. 7 as well, for details of the diagnostics and adaptive control method 200, for detection of coking in aircraft fuel initially as shown at 205 generating an excitation signal to the fuel contamination sensor 62 disposed in a fuel system 60 on a gas turbine engine 20. The sensor measurements from sensor 62 are received by the controller 106 of the engine control system as shown at process step 210. At step 215 a comparison of the received sensor signal and the excitation signal is initiated. In an embodiment, the comparison includes looking at phases, or frequency shift imposed by the build of contamination on the sensor 62. Continuing with the method 200 at process step 220 the condition of the fuel is diagnosed based on the comparisons. In one embodiment, any indication of contamination may be identified as a sufficient to determine that coking is present in the fuel, in another embodiment, multiple detections may be required. In another embodiment, a number of detections beyond a selected duration may be sufficient. For example, detection of contamination for a number of seconds or minutes. Moreover, periodic measurements of the "dirty" fuel provide data points trending away from the established "baseline" measurement for clean jet fuel. "Dirty" fuel can be defined as any jet fuel that has an increased mass fraction of non-liquid carbonaceous deposits (i.e. coking sludge, varnish, gum, etc.). This provides additional "historical data" that can be used for lifetime predictions of fuel components exposed to the contaminated jet fuel.

To avoid frequent "nuisance faults" in an embodiment, the fuel contamination sensor 62 may be designed to signal the engine's control system as described below and aircraft on-board computers only after a certain predetermined threshold of coke/varnish has been accumulated. This input can be synchronized with the on-board Prognostics and Health Management (PHM) to provide predictive diagnostics for preventive engine maintenance. For example, in one embodiment, when a preset threshold is reached during operation of the engine, the signal can set a latched input which upon WOW=1 (i.e. weight on wheels, upon aircraft landing) remains latched until the ground maintenance crew cleans/replaces the clogged fuel plug 63 with the fuel contamination sensor 62 and inspects the fuel system 60 for varnish/coke deposits. Upon completion of the necessary repair/replacement, the signal is unlatched in the PHM system.

Finally, at process step 225, a fault is indicated to an operator or ground/maintenance personnel to ensure that the fuel system is inspected. Detection of coking may result in required cleaning and servicing of the fuel system, particularly for gas turbine engines.

Advantageously, the described embodiments provided technical benefits of early detection and warning about the start of coking/varnishing in jet fuel. In addition, such detection permits pro-active preventive maintenance due to PHM trending. As a result, the gas turbine engine exhibits improved reliability of fuel-immersed components and systems. Finally, as an overall system, the fuel system can provide enhanced capabilities as a heat sink at elevated fuel temperatures because coking can be directly detected and addressed with more immediate corrective action.

In terms of hardware architecture, such a computing device can include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and receivers to enable communications. Further, the local interface may include address, control, and/or data connections to enable appropriate communications among the aforementioned components.

When the computing device is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed. The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set), or generally any device for executing software.

The memory can include any one or combination of volatile memory elements (e.g., random access memory (RAM, such as DRAM, SRAM, SDRAM, VRAM, etc.)) and/or nonvolatile memory elements (e.g., ROM, hard drive, tape, CD-ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, such as a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance, but not limited to, a modulator/demodulator (modem; for accessing another device, system, or network), a radio frequency (RF) or other transceiver, a telephonic interface, a bridge, a router, etc.

One should note that the FIGS. 6 and 7 show the architecture, functionality, and/or operation of a possible implementation of software. In this regard, one or more of the blocks can be interpreted to represent a module, segment, or portion of code, which comprises one or more executable instructions for implementing the specified logical function(s). It should also be noted that in some alternative implementations, the functions noted in the blocks may occur out of the order and/or not at all. For example, two blocks shown in succession may in fact be executed substantially concurrently or the blocks may sometimes be executed in the reverse order, depending upon the functionality involved.

One should note that any of the functionality described herein can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" contains, stores, communicates, propagates and/or transports the program for use by or in connection with the instruction execution system, apparatus, or device. The computer readable medium can be, for example but not limited to, an electronic, magnetic, optical, electromagnetic, infrared, or semiconductor system, apparatus, or device. More specific examples (a non-exhaustive list) of a computer-readable medium include a portable computer diskette (magnetic), a random access memory (RAM) (electronic), a read-only memory (ROM) (electronic), an erasable programmable read-only memory (EPROM or Flash memory) (electronic), and a portable compact disc read-only memory (CDROM) (optical).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A method for early detection of coking in aircraft fuel in a fuel system, the method comprising:
   generating an excitation signal for a contamination detection sensor having an input transducer and an output transducer immersed in the aircraft fuel;
   receiving at a controller operably connected to the contamination detection sensor a sensor output signal from the output transducer;
   comparing the sensor output signal with the excitation signal;
   diagnosing a condition of the fuel based on a the comparing; and
   indicating a condition of coking based on the diagnosing, wherein the diagnosing includes at least one of collecting data over time to facilitate making lifetime predictions of fuel system component, and identifying coking only after a predetermined threshold of coking has been exceeded.

2. The method of claim 1, wherein the generating includes providing an alternating current (AC) signal to the contamination detection sensor.

3. The method of claim 2, wherein the alternating current (AC) signal is at least one of a sinusoid and exhibits a frequency corresponding to the synchronous frequency of the contamination detection sensor to minimize insertion loss.

4. The method of claim 1, wherein the contamination detection sensor is at least one of a surface acoustic wave sensor, a horizontal shear acoustic wave sensor, and a thickness shear mode sensor.

5. The method of claim 1, wherein the sensor output signal exhibits at least one of a delay, a phase shift, a frequency shift based on a presence of particulates in the aircraft fuel.

6. The method of claim 5, wherein the at least one of a delay, a phase shift, and a frequency shift is proportional to the mass of a particle or film deposited on the sensor in the aircraft fuel.

7. The method of claim 1, wherein the identifying includes latching an indication of detected coking and notifying a ground maintenance to conduct and inspection of the fuel system.

8. The method of claim 1, wherein the fuel system includes at least one of sensors, valves, tubing nozzles, and injectors.

9. A system for early detection of coking in aircraft fuel, the system comprising:
   a fuel system for delivery of fuel to a component;
   a fuel contamination sensor, the fuel contamination sensor comprising a contamination detection sensor having an input transducer and an output transducer immersed in the aircraft fuel;
   a controller in operable communication with the fuel contamination sensor, the controller configured to execute a method for early detection of coking in the aircraft fuel, the method comprising:
      generating an excitation signal for the contamination detection sensor;
      receiving at a controller operably connected to the contamination detection sensor a sensor output signal from the output transducer;
      comparing the sensor output signal with the excitation signal;
      diagnosing a condition of the fuel based on a the comparing;
      indicating a condition of coking based on the diagnosing; and
   an enunciator to indicate the detection of coking,
   wherein the diagnosing includes at least one of collecting data over time to facilitate making lifetime predictions of fuel system component, and identifying coking only after a predetermined threshold of coking has been exceeded.

10. The system of claim 9, wherein the excitation signal is an alternating current (AC) signal to the contamination detection sensor.

11. The system of claim 10, wherein the alternating current (AC) signal is at least one of a sinusoid and exhibits a frequency corresponding to the synchronous frequency of the contamination detection sensor to minimize insertion loss.

12. The system of claim 9, wherein the contamination detection sensor is at least one of a surface acoustic wave sensor, a horizontal shear acoustic wave sensor, and a thickness shear mode sensor.

13. The system of claim 9, wherein the sensor output signal exhibits at least one of a delay, a phase shift, a frequency shift based on a presence of at least one of particulates and film disposed on the contamination detection sensor in the aircraft fuel.

14. The system of claim 9, wherein the output signal of the sensor exhibits at least one of a delay, a phase shift, and a frequency shift proportional to the mass of a particle or film deposited on the sensor in the aircraft fuel.

15. The system of claim 9, wherein the identifying includes latching an indication of detected coking and generating a notification to conduct and inspection of the fuel system.

16. The system of claim 9, wherein the fuel system components include at least one of sensors, valves, tubing nozzles, and injectors.

17. The system of claim 9, wherein at least a portion of the fuel system is used as a heat sink.

18. The system of claim 9, wherein the fuel system is part of a gas turbine engine.

19. A system for early detection of coking in aircraft fuel, the system comprising:

a fuel system for delivery of fuel to a component;
a fuel contamination sensor, the fuel contamination sensor comprising a contamination detection sensor having an input transducer and an output transducer immersed in the aircraft fuel;
a controller in operable communication with the fuel contamination sensor, the controller configured to execute a method for early detection of coking in the aircraft fuel, the method comprising:
generating an excitation signal for the contamination detection sensor;
receiving at a controller operably connected to the contamination detection sensor a sensor output signal from the output transducer;
comparing the sensor output signal with the excitation signal;
diagnosing a condition of the fuel based on a the comparing;
indicating a condition of coking based on the diagnosing; and
an enunciator to indicate the detection of coking,
wherein the identifying includes latching an indication of detected coking and generating a notification to conduct and inspection of the fuel system.

* * * * *